United States Patent [19]
Blinn

[11] Patent Number: 5,640,973
[45] Date of Patent: Jun. 24, 1997

[54] METHOD OF USING A CONDOM WITH DISTAL APERTURE

[76] Inventor: Lawrence P. Blinn, 211 Jewett Rd., Upper Nyack, N.Y. 10960

[21] Appl. No.: 411,864

[22] Filed: Mar. 28, 1995

Related U.S. Application Data

[63] Continuation of Ser. No. 229,902, Apr. 19, 1994, abandoned.
[51] Int. Cl.$^6$ ...................................................... A61F 6/04
[52] U.S. Cl. ............................................ 128/844; 128/918
[58] Field of Search ........................... 128/844, 842, 128/918; 604/347, 349

[56] References Cited

U.S. PATENT DOCUMENTS

| | | | |
|---|---|---|---|
| 2,410,460 | 11/1946 | Robinson | 128/844 |
| 2,636,492 | 4/1953 | Weight | 128/844 |
| 3,018,484 | 1/1962 | Koehn | 128/844 |
| 3,401,696 | 9/1968 | O'Brien | 604/347 |
| 4,332,243 | 6/1982 | Gutnick | 128/844 |
| 4,498,466 | 2/1985 | Pomeranz | 604/347 |
| 4,527,988 | 7/1985 | Lutz et al. | 604/349 |
| 4,626,250 | 12/1986 | Schneider | 604/347 |
| 4,872,463 | 10/1989 | Nishizono | 128/844 |
| 5,050,619 | 9/1991 | Ferguson | 128/844 |
| 5,070,890 | 12/1991 | Papurt | 128/844 |

FOREIGN PATENT DOCUMENTS 9417760  8/1994  WIPO ................................ 128/844

Primary Examiner—Jessica Harrison
Assistant Examiner—Michael O'Neill
Attorney, Agent, or Firm—Morgan & Finnegan

[57] ABSTRACT

A condom that includes a small hole in the distal or far end to permit semen to pass out of the interior of the condom. The condom may be used by couples wishing to conceive a child but who want to reduce the risk that a disease or virus, etc. will be passed from one person to the other. A second embodiment includes a removable cover over the distal opening to reduce the time during which the hole is uncovered. A cord attached to the cover can be pulled to remove the cover from the distal hole immediately before ejaculation.

2 Claims, 2 Drawing Sheets

METHOD OF USING A CONDOM WITH DISTAL APERTURE

This is a continuation of application Ser. No. 08/229,902, filed on Apr. 19, 1994, now abandoned.

FIELD OF THE INVENTION

This invention relates to a condom that can be used by couples to reduce the risk of transmitting a sexually transmitted disease and, more particularly, to a such a condom that will not prevent pregnancy.

BACKGROUND OF THE INVENTION

Condoms have been widely used for many years as a form of birth control since sperm ejaculated by a male is trapped inside the condom preventing the sperm from contacting the female and fertilizing an egg. Another benefit of condoms relates to the reduced risk of the transmission of a sexually transmitted disease since a properly used condom will minimize or eliminate entirely the exchange of fluids that usually accompanies intercourse. Latex condoms have been found to be particularly useful for this purpose.

For couples where one partner has a particular sexually transmitted disease, condoms are advisable to reduce the risk of infecting the uninfected person. However, when such couples desire to conceive a child, their use of condoms will have the undesirable effect of preventing pregnancy.

SUMMARY OF THE INVENTION

The disadvantages associated with the prior art have been overcome by the present invention which provides a condom having an aperture in its far or distal end, allowing sperm to exit the condom.

In one aspect, the invention features a condom for reducing the risk of the transmission of a disease while permitting the passage of sperm out of the condom, the condom comprising a substantially cylindrical tube having distal and proximal ends, a first opening located at the proximal end of the tube for receiving a penis, and a second opening located at the distal end of the tube for permitting sperm to pass out of the tube.

The tube is preferably formed of a flexible material such as latex and the second opening is substantially small than the first opening. The second opening is preferably round.

A removable covering can be attached to the distal end of the tube over the second opening. A cord can be attached to the covering to permit a user to remove the covering from the second opening at a desired time (e.g., immediately prior to ejaculation). The cord can be guided to the proximal end of the condom using a longitudinally extending hollow passageway formed in the outer wall of the condom.

The invention allows a couple who want to conceive a child to obtain the benefits of protection from the spread of venereal disease without inhibiting their chances of having a child. The invention will be more clearly understood from the following detailed description of two embodiments of the invention.

DETAILED DESCRIPTION OF THE PREFERRED EMBODIMENTS

Figure 1:
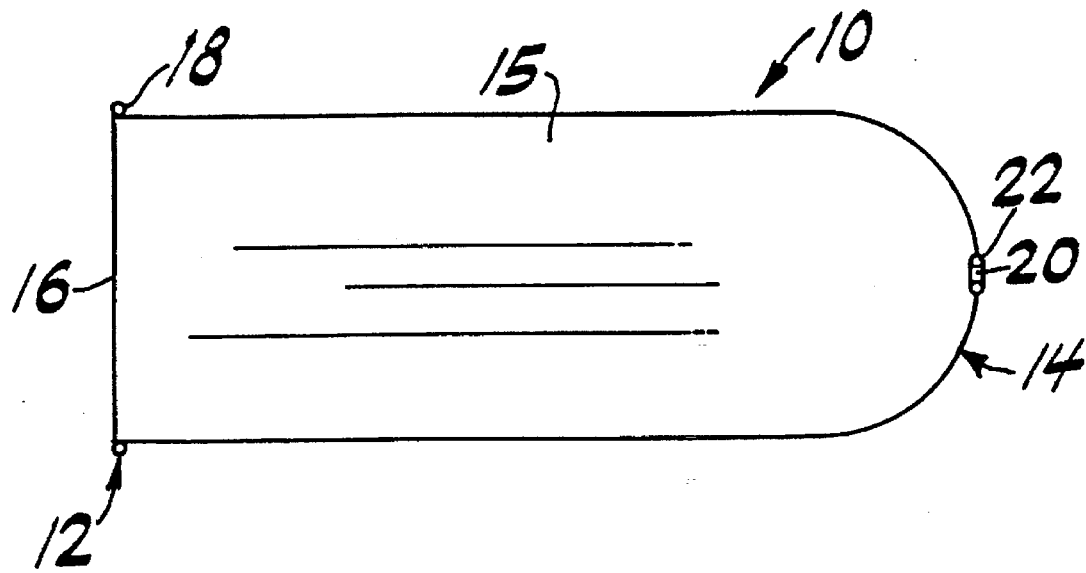
FIG. 1 is a cross-sectional view of a first embodiment of a condom according to the present invention.

Referring to FIG. 1, a condom 10 is illustrated in cross-section and includes a proximal end 12 and a distal end 14. The condom includes a tubular member 15 of elastomeric material, preferably latex. A first opening 16 is formed in the proximal end 12 for receiving a penis, as is standard and well known in the condom art. A reinforced ring 18 is attached to the outer perimeter of tubular member 15 at proximal end 18 to reinforce the condom and provide elastic fit around the penis.

Located at the distal end 14 is a second, smaller opening 20 in the form of a circular hole. A reinforcing ring 22 defines the hole and is attached to tubular member 15. Ring 22 prevents tears in the tubular member 15.

Figure 2:
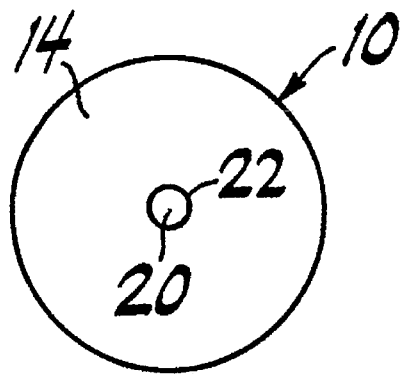
FIG. 2 is an end view of the condom shown in FIG. 1.

FIG. 2 shows an end view of the distal portion 14 of condom 10. Hole 20 can be seen as providing a passageway between the interior of the condom and the exterior of the condom.

In use, the condom is placed on the penis prior to sexual intercourse in the usual manner. Hole 20 permits semen to pass from the condom during ejaculation, thus enabling the female to become impregnated.

Figure 3:
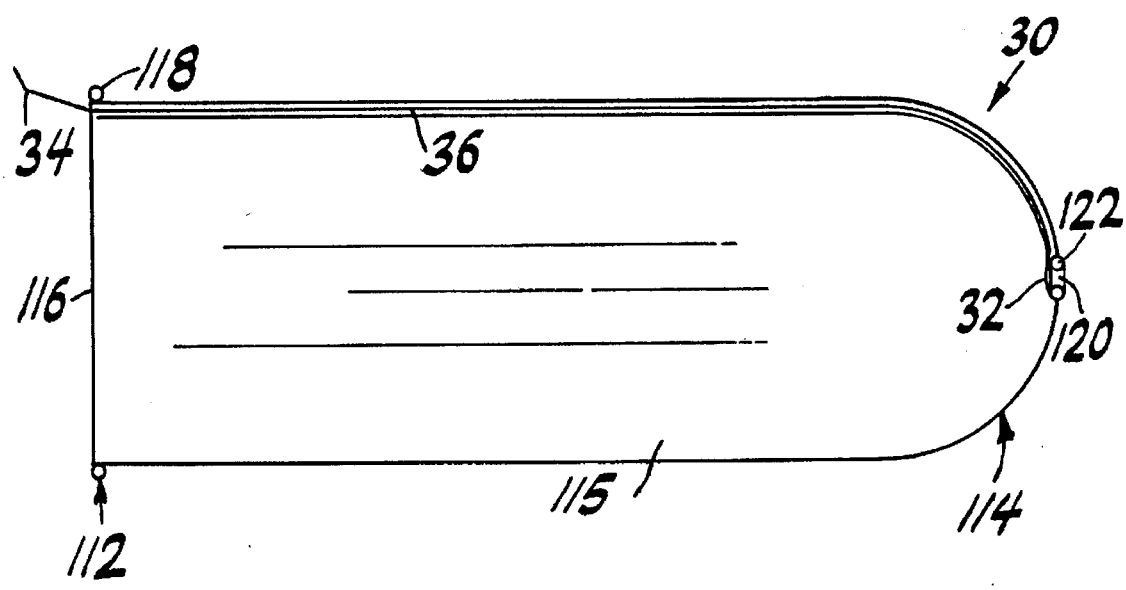
FIG. 3 is a cross-sectional view of a second embodiment of a condom according to the present invention.

Referring to FIG. 3, a second embodiment of the invention is illustrated. A condom 30 is shown and includes distal end 114, proximal end 112, first opening 116 and second opening 120. Reinforcing rings 118, 122 are also found in condom 30. Unlike condom 10 illustrated in FIGS. 1–2, condom 30 includes a removable covering 32 that covers opening 120 of the condom. Covering 32 has one end of a cord 34 attached to it, with the other end of cord 34 passing out of the proximal end of the condom. Cord 34 travels from covering 32 to the proximal end 112 of condom 30 through a passageway 36 formed in the condom wall.

Figure 4:
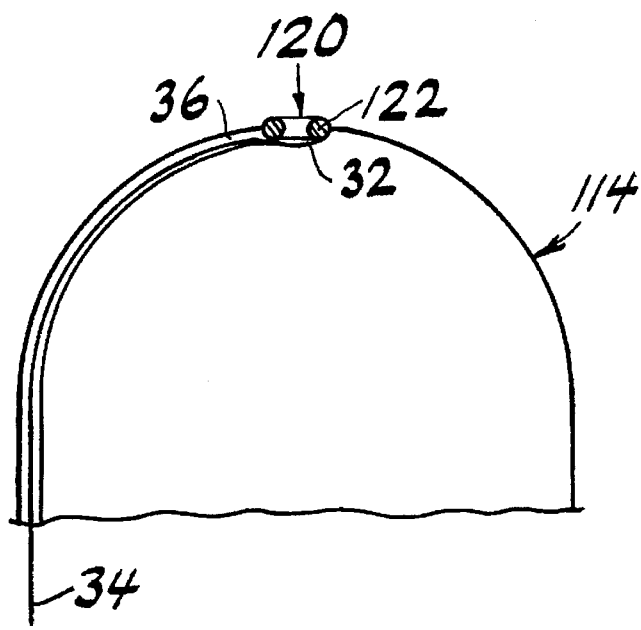
FIG. 4 is an enlarged cross-sectional view of a portion of the condom shown in FIG. 3.

FIG. 4 is an enlarged view of the distal end 114 of condom 30 and shows covering 32 in greater detail. Covering 32 is directly attached to reinforcing ring 122 by a suitable method, such as with an adhesive. In use, cord 34 can be pulled just prior to ejaculation to uncover hole 120 thereby enabling semen to escape from the interior of the condom.

The embodiment of FIGS. 3–4 will reduce the period of time during which the distal hole serves as a passageway for fluids, thereby further reducing the risk that an unwanted virus or disease, etc., will be passed from one partner to the other.

The invention also has the advantage of reducing the likelihood of the transmission of STDs that are transmitted by skin contact, such as genital warts and herpes. Both partners would be less likely to suffer exposure to these conditions since the skin to skin contact during intercourse is significantly reduced due to the condoms of the present invention.

It will be understood by those skilled in the art that the above embodiments are merely illustrative of the invention and that modifications may be made within the scope of the appended claims. For example, the distal hole need not be circular and the condom itself need not be cylindrical. Any shape condom could be used as long as it fits and will remain in place during intercourse.

The distal hole may also be in the form of a one way valve that permits fluid to exit the condom, but does not allow fluid to enter the condom. As defined herein, and as used in the claims appended hereto, the word "opening" requires only that fluid be able to pass therethrough in at least one direction.

We claim:

1. A method for reducing the chance of contacting at least one of venereal warts and herpes simplex vesicles on at least one of a penis shaft, glans and vaginal wall while permitting the passage of sperm from said penis into said vagina, said method comprising the steps of:

a) providing a substantially cylindrical tube of flexible material wherein said tube has a first opening located at a proximal end of said tube for receiving said penis, and a second substantially smaller opening located at a distal end of said tube for permitting sperm to pass out of said tube and into said vagina during intercourse;

b) placing said tube over said penis shaft and glans before intercourse; and c) commencing intercourse with said tube in place.

2. The method of claim 1 wherein said tube is formed of latex.

* * * * *